United States Patent
el Kaliouby et al.

(10) Patent No.: US 9,934,425 B2
(45) Date of Patent: Apr. 3, 2018

(54) COLLECTION OF AFFECT DATA FROM MULTIPLE MOBILE DEVICES

(71) Applicant: Affectiva, Inc., Waltham, MA (US)

(72) Inventors: Rana el Kaliouby, Boston, MA (US); Daniel Abraham Bender, Cambridge, MA (US); Evan Kodra, Waltham, MA (US); Oliver Ernst Nowak, Medford, MA (US); Richard Scott Sadowsky, Sturbridge, MA (US); Thibaud Senechal, Cambridge, MA (US); Panu James Turcot, San Francisco, CA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 14/144,413

(22) Filed: Dec. 30, 2013

(65) Prior Publication Data

US 2014/0112540 A1    Apr. 24, 2014

Related U.S. Application Data

(63) Continuation-in-part of application No. 13/153,745, filed on Jun. 6, 2011, now abandoned, and a
(Continued)

(51) Int. Cl.
  *G06K 9/00* (2006.01)
  *A61B 5/16* (2006.01)
  (Continued)

(52) U.S. Cl.
  CPC .......... *G06K 9/00302* (2013.01); *A61B 5/165* (2013.01); *G06F 19/3418* (2013.01);
  (Continued)

(58) Field of Classification Search
  CPC ........... G06K 9/00275; G06K 9/00281; G06K 9/0028; G06K 9/00295; G06K 9/00302;
  (Continued)

(56) References Cited

U.S. PATENT DOCUMENTS 3,034,500 A    5/1962    Backster, Jr.
3,548,806 A    12/1970   Fisher
(Continued)

FOREIGN PATENT DOCUMENTS

JP    08115367        7/1996
JP    2010028605 A    2/2010
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

A user interacts with various pieces of technology to perform numerous tasks and activities. Reactions can be observed and mental states inferred from these performances. Multiple devices, including mobile devices, can observe and record or transmit a user's mental state data. The mental state data collected from the multiple devices can be used to analyze the mental states of the user. The mental state data can be in the form of facial expressions, electrodermal activity, movements, or other detectable manifestations. Multiple cameras on the multiple devices can be usefully employed to collect facial data. An output can be rendered based on an analysis of the mental state data.

35 Claims, 5 Drawing Sheets

Related U.S. Application Data continuation-in-part of application No. 14/064,136, filed on Oct. 26, 2013, now Pat. No. 9,204,836, and a continuation-in-part of application No. 13/153,745, filed on Jun. 6, 2011, now abandoned.

(60) Provisional application No. 61/747,651, filed on Dec. 31, 2012, provisional application No. 61/747,810, filed on Dec. 31, 2012, provisional application No. 61/793,761, filed on Mar. 15, 2013, provisional application No. 61/789,038, filed on Mar. 15, 2013, provisional application No. 61/798,731, filed on Mar. 15, 2013, provisional application No. 61/844,478, filed on Jul. 10, 2013, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/719,383, filed on Oct. 27, 2012, provisional application No. 61/790,461, filed on Mar. 15, 2013.

(51) Int. Cl.

| | | |
|---|---|---|
| *G06F 19/00* | (2018.01) | |
| *G06Q 30/02* | (2012.01) | |
| *A61B 5/0205* | (2006.01) | |
| *A61B 5/024* | (2006.01) | |
| *A61B 5/053* | (2006.01) | |
| *A61B 5/08* | (2006.01) | |
| *A61B 5/11* | (2006.01) | |
| *G06Q 50/00* | (2012.01) | |

(52) U.S. Cl.
CPC ..... *G06F 19/3481* (2013.01); *G06Q 30/0271* (2013.01); *A61B 5/02055* (2013.01); *A61B 5/02405* (2013.01); *A61B 5/0533* (2013.01); *A61B 5/08* (2013.01); *A61B 5/11* (2013.01); *G06Q 50/01* (2013.01)

(58) Field of Classification Search
CPC ........... G06K 9/00308; G06K 9/00315; G06K 9/00335; G06K 9/00342; G06K 9/00348; G06K 9/00355; G06K 9/00362; G06K 9/00241
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstrom et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |

(56) References Cited

U.S. PATENT DOCUMENTS

| | | |
|---|---|---|
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,401,248 B1 | 3/2013 | Moon et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1* | 11/2002 | Eshelman et al. ......... 340/573.1 |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0078513 A1 | 4/2003 | Marshall |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer et al. |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1 | 6/2006 | Mori |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1* | 11/2008 | Kurtz ...................... A61B 3/10 382/128 |
| 2009/0002178 A1 | 1/2009 | Guday et al. |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0123776 A1* | 5/2010 | Wydeven ............... H04N 7/183 348/77 |
| 2010/0266213 A1 | 10/2010 | Hill |
| 2010/0274847 A1* | 10/2010 | Anderson et al. ............ 709/203 |
| 2011/0092780 A1 | 4/2011 | Zhang et al. |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0263946 A1* | 10/2011 | el Kaliouby et al. ........ 600/300 |
| 2011/0301433 A1 | 12/2011 | Sadowsky et al. |
| 2012/0124122 A1 | 5/2012 | el Kaliouby et al. |
| 2012/0293548 A1 | 11/2012 | Perez et al. |
| 2012/0304206 A1 | 11/2012 | Roberts et al. |
| 2012/0324491 A1 | 12/2012 | Bathiche et al. |
| 2013/0023337 A1 | 1/2013 | Bowers et al. |
| 2013/0102854 A1* | 4/2013 | Zheng et al. .................. 600/300 |
| 2014/0112540 A1* | 4/2014 | el Kaliouby et al. ........ 382/103 |
| 2014/0200416 A1* | 7/2014 | Kashef et al. ................. 600/301 |
| 2014/0200417 A1* | 7/2014 | Senechal et al. ............. 600/301 |
| 2014/0200463 A1* | 7/2014 | el Kaliouby et al. ........ 600/484 |
| 2014/0201207 A1* | 7/2014 | Sadowsky et al. ........... 707/736 |
| 2014/0323817 A1* | 10/2014 | el Kaliouby et al. ........ 600/300 |
| 2014/0357976 A1* | 12/2014 | Pitre et al. .................... 600/407 |

FOREIGN PATENT DOCUMENTS

| | | |
|---|---|---|
| KR | 10-2005-0021759 A | 3/2005 |
| KR | 10-2008-0016303 A | 2/2008 |
| KR | 1020100001409 A | 1/2010 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

International Search Report dated Apr. 22, 2015 for PCT/US2013/78380.

Albiol, Alberto, et al. "Face recognition using HOG-EBGM." Pattern Recognition Letters 29.10 (2008): 1537-1543.

* cited by examiner

COLLECTION OF AFFECT DATA FROM MULTIPLE MOBILE DEVICES

RELATED APPLICATIONS

This application claims the benefit of U.S. provisional patent applications "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Sporadic Collection of Mobile Affect Data" Ser. No. 14/064,136, filed Oct. 26, 2012, which claims the benefit of U.S. provisional patent applications "Sporadic Collection of Affect Data" Ser. No. 61/719,383, filed Oct. 27, 2012, "Optimizing Media Based on Mental State Analysis" Ser. No. 61/747,651, filed Dec. 31, 2012, "Collection of Affect Data from Multiple Mobile Devices" Ser. No. 61/747,810, filed Dec. 31, 2012, "Mental State Analysis Using Heart Rate Collection Based on Video Imagery" Ser. No. 61/793,761, filed Mar. 15, 2013, "Mental State Data Tagging for Data Collected from Multiple Sources" Ser. No. 61/790,461, filed Mar. 15, 2013, "Mental State Analysis Using Blink Rate" Ser. No. 61/789,038, filed Mar. 15, 2013, "Mental State Well Being Monitoring" Ser. No. 61/798,731, filed Mar. 15, 2013, and "Personal Emotional Profile Generation" Ser. No. 61/844,478, filed Jul. 10, 2013. This application is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to analysis of mental states collected from multiple sources.

BACKGROUND

People spend an ever-increasing amount of time interacting with computers, and consume a vast amount of computer-delivered media. This interaction may be for many different reasons, such as to obtain educational content, to be entertained and find sources of entertainment, to interact using social media, to create documents, and to play games, to name a few.

In some cases, the human-computer interaction may take the form of a person performing a task using a software-based tool running on a computer. Examples may include creating a document, editing a video, and/or doing one or more of the numerous other activities performable by a modern computer. The person may find the execution of certain activities interesting or even exciting, and may be surprised at how easy it is to perform the activity. The person may become excited, happy, or content as he or she performs an activity. On the other hand, the person may find some activities difficult to perform, and may become frustrated or even angry with the computer or software tool. In some cases, users may be surveyed in an attempt to determine whether a computer or computer program functioned well, for example, as well as to identify where the computer program may need improvement. However, such survey results are often unreliable because the surveys are often completed well after the activity was performed. In addition, survey participation rates may be low, and people may not provide accurate and honest answers to the survey.

In other cases of human-computer interaction, the person may not be using a software tool to accomplish a task, but instead may be consuming computer-accessed content or media, such as news, pictures, music, or video. Currently, people consuming computer-driven content may tediously self-rate the media to communicate personal preferences. In some cases, viewers enter a specific number of stars corresponding to a level of like or dislike, while in other cases, users are asked to answer a list of questions. While such a system of evaluation may be a helpful metric by which to evaluate media and other products or services, the evaluation may also prove tedious and challenging. Thus, in many cases, this type of subjective evaluation is neither a reliable nor practical way to evaluate personal responses to media. Recommendations based on such a system of star rating and/or other means of self-reporting are imprecise, subjective, unreliable, and are further limited by sample size, as, in past experiences, only a small number of viewers have proven to actually rate the media they consume.

SUMMARY

Consumers interact with multiple computing devices in a variety of tasks and/or activities. In response to such an interaction, a user will react with a specific mental state. Such a mental state can express itself in one or more of many ways such as facial expressions, electrodermal activity, movements, or other externally detectable manifestations. Multiple cameras and/or other monitoring devices—that, individually or collectively, may be referred to as a sensor or sensors—can be used to capture one or more of the externally detectable manifestations of the user's mental state.

However, there can be conditions where one or more of the monitoring devices are not able to continually detect the manifestation. Thus, various methods, computer program products, apparatus, and systems wherein mental state data is collected by multiple sensors, analyzed, and an output rendered based on the analysis of the mental state data are described herein. A computer-implemented method for mental state analysis is disclosed comprising: obtaining mental state data which is collected on an individual from multiple sources wherein the multiple sources include at least two sources of facial data; obtaining analysis of the mental state data which is collected from the multiple sources; and rendering an output based on the analysis of the mental state data. The mental state data from multiple sources can be tagged. Analysis can include aggregating the mental state data from the multiple sources.

In embodiments, a computer program product embodied in a non-transitory computer readable medium for mental state analysis comprises: code for obtaining mental state data which is collected on an individual from multiple sources wherein the multiple sources include at least two sources of facial data; code for obtaining analysis of the mental state data which is collected from multiple sources; and code for rendering an output based on the analysis of the mental state data. In some embodiments, a computer system for mental state analysis comprises: a memory which stores instructions; one or more processors coupled to the memory wherein the one or more processors, when executing the instructions which are stored, are configured to: obtain mental state data which is collected on an individual from multiple sources wherein the multiple sources include at least two sources of facial data; obtain analysis of the mental state data which is collected from multiple sources; and render an output based on the analysis of the mental state data. In embodiments, a computer-implemented method for mental state analysis comprises: receiving mental state data which is collected on an individual from multiple sources wherein the multiple sources include at least two sources of facial data; analyzing the mental state data which is collected from multiple sources; and providing the analysis of the mental state data to a client machine. In some embodiments, a computer-implemented method for mental state analysis comprises: receiving analysis of mental state data which is collected on an individual from multiple sources wherein the multiple sources include at least two sources of facial data; and rendering an output based on the analysis of the mental state data. In embodiments, a computer-implemented method for mental state analysis may comprise: collecting mental state data on an individual from multiple sources wherein the multiple sources include at least two sources of facial data; analyzing the mental state data which is collected from multiple sources; and rendering an output based on the analysis of the mental state data.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
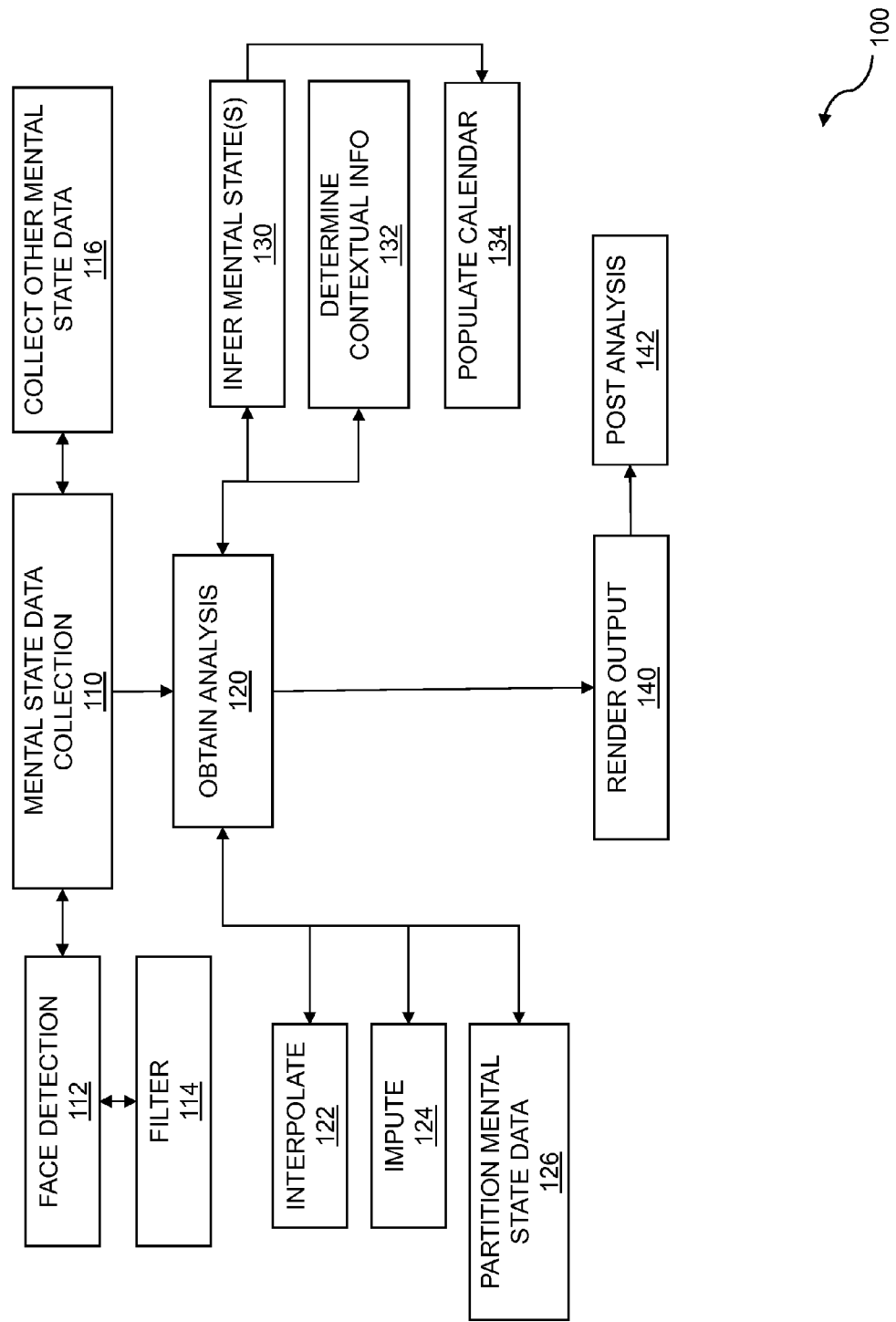
FIG. 1 is a flow diagram for mental state analysis.

As a user interacts with one or more of various computing devices, the user's mental state can provide valuable insight into the nature of the human-computer interaction. The mental state of the user can include such emotions as frustration, confusion, disappointment, hesitation, cognitive overload, fear, exhaustion, focus, engagement, attention, boredom, exploration, confidence, trust, delight, satisfaction, excitement, happiness, contentment, or many other human emotions. Understanding a user's mental state as he or she interacts with the computing devices can be valuable for a variety of reasons, such as determining which aspects of a computer program are functioning as intended and which aspects require further improvement; determining aspects of a computer game that are too difficult for some users or are easy for some users; measuring the effectiveness of advertisements; determining which parts of a video most please a specific user; or determining a user's preferences in order to better suggest what other media, games, or applications the specific user may find appealing, to name a few potential applications.

While consuming media, the user can exhibit physical manifestations of his or her mental state, such as facial expressions, physiological reactions, and movements. Sensors coupled to a computer—in some embodiments, the same computer with which the user is interacting; in other embodiments, one or more other computers—are able to detect, capture, and/or measure one or more external manifestations of the user's mental state. For example, a still camera can capture images of the user's face; a video camera can capture images of the user's movements; a heart rate monitor can measure the user's heart rate; a skin resistance sensor can detect changes in the user's galvanic skin response; and an accelerometer can measure such movements as gestures, foot tapping, or head tilts, to name a few. In embodiments, multiple sensors to capture the user's mental state data are included.

However, depending on the user and/or the sensor, certain embodiments allow the continuous capture of all of the manifestations of mental states under observation. For example, when a user looks away from the camera, certain embodiments render the capture of images of the face of the user impossible until they look back at the camera. As a further example, a skin conductance sensor embedded in an armrest of the user's chair can only measure a galvanic skin response if the user's arm is resting on the armrest. In other cases, continuous data capture from a given sensor is a possibility, but such capture may not be practical or desirable due to the sheer volume of data or other factors.

Thus, as a user interacts with a cell phone, a laptop, a tablet, and other computing devices, or as images of the user are captured through various other cameras, mental state data can be collected through facial image capture. By combining the results of these variously captured images, the mental states of one person can be analyzed using input from multiple sources. The combination of multiple sources can allow a more thorough coverage and capture of data, thereby making it possible to provide higher quality mental state analysis. In some cases, images from a camera can be saved for further analysis based on pre-processing where a user's face is detected as being visible in the image.

Once the data has been collected from the multiple devices, an analysis of the mental state data is obtained. The analysis can take place on the computer with which the user is interacting, the computer or computers that captured the sensor data, and/or from one or more other computers that are local or remote to the user. The analysis can provide the mental states of the user over time based on the sensor data. During some periods, data from more than one sensor is available and can be used together with data from other sensors to provide a continuous rendering of the user's mental state information. During other periods, data from one particular sensor is available and can provide continuous mental state information for the user. Further, during still other periods, data from another particular sensor is used to provide mental state information for the user. In some cases, the mental state of the user can be estimated, interpolated, or inferred for the periods where data from one or more sensors was not collected.

After the analysis of the mental state data has been obtained, an output based on the analysis is rendered. The rendered output can include text, icons, pictures, graphs, binary data, or any other form or output that a person or another computer can interpret, depending on the embodiment. In at least one embodiment, the rendered output includes a graph showing the prevalence of a particular mental state over time. In some embodiments, the rendered output includes an icon that changes based on the user's mental state. In some embodiments, the rendered output includes a file containing numerical data based on the obtained analysis. The result of the mental state analysis can also be included in a calendar where it can be displayed or compared with the ongoing activities already included in the calendar.

FIG. 1 is a flow diagram 100 for mental state analysis comprising a computer-implemented method for mental state analysis. The flow 100 includes obtaining mental state data 110 which is collected from multiple sources on an individual wherein the multiple sources include at least two sources of facial data. In embodiments, the multiple sources include multiple cameras, each positioned with a different view of the user. In some embodiments, the multiple sources include at least one mobile device. Any type of image capture device can be used as a source of facial data, including a webcam, a video camera, a still camera, a thermal imager, a CCD device, a phone camera, a three-dimensional camera, a depth camera, multiple webcams used to show different views of a person, or any other type of image capture apparatus that can allow data captured to be used in an electronic system. In some embodiments, the facial data is collected intermittently when the individual is looking in a direction of a camera, although there may be times when facial data is not captured because the user's face is not visible to any cameras. The flow 100 further comprises performing face detection 112 to determine whether the individual is looking towards a camera of one of the multiple devices. The flow 100 further comprises filtering out faces 114 of one or more other people to determine whether the individual is looking toward a camera of one of the multiple devices. By using the facial image information from multiple devices, more comprehensive mental state data can be collected.

The flow 100 further comprises collecting other mental state data 116 from the individual on a continuous basis, or, in some embodiments, on an intermittent basis. Other mental state data can include any type of mental state data including, but not limited to, heart rate, respiration rate, blood pressure, skin resistance, audible sounds, gestures, or any other type of data that can be useful for determining mental state information. Thus in some embodiments, the other mental state data includes electrodermal activity data.

The flow 100 includes obtaining analysis 120 of the mental state data collected from multiple sources. In some embodiments, obtaining analysis includes performing the analysis on a local computer, which may be the computer that collected the mental state data and/or a computer with which a user being monitored is interacting. In some embodiments, the obtaining of analysis includes performing the analysis on a local server, a quasi-local server—for example, a server in the same building or campus as the user being monitored—or on a remote server. In some embodiments, the obtaining analysis includes receiving the analysis from another computer, such as a local or remote server, which can be a web service. Thus in some embodiments, the analysis of the mental state data is obtained from a web service. Because the mental state data can be collected using multiple sources, the analysis can include aggregating the mental state data from the multiple sources. Mental state data can be stitched together from the various sources and the stitching may occur at a web service. Stitching can include using mental state data, or analysis from the mental state data, from multiple sources to provide a more complete picture of the emotional experiences of the individual. In some embodiments, analysis includes identifying a best view where two or more of the multiple sources have a camera with a view of the individual. Mental state data from the best view may be used or given priority in the obtaining of the analysis. The best view, in most cases the front view of the face, is then used in mental state analysis. The flow 100 further comprises interpolating 122 mental state data and/or mental state analysis where the mental state data collected is intermittent. In some embodiments, the interpolating can be done between data sets collected from different sources. The flow may include assembling the mental state data from the multiple sources at a web service, analyzing the mental state data to provide mental state information, and using the mental state information, based on the mental state data from the multiple sources to infer mental states.

The flow 100 further comprises imputing 124 additional mental state data where the mental state data is missing. The imputing can include filling in blanks where data has not been collected, estimating between points in time where data has been collected, extrapolating from a previously collected data point, or the like. Analysis, based on the multiple sources of mental state data, can be used in market research. In some cases, an advertisement can be sent to an individual on a specific device, based on data obtained from that device and other devices. Using the multiple devices, a neutral mental state can be determined from one device and an advertisement or other media presentation can be sent to that or another device. Further, a specific mood or emotional state can be targeted and watched for across the various devices. When that mood is detected, an advertisement or media presentation can be sent to a desired device.

The flow further comprises partitioning the mental state data 126 based on tagging. Tags can include various types of information including metadata related to the mental state data, the user being monitored, the device that captured the mental state data, or other types of data. The mental state data from multiple sources can be tagged with information identifying the source that captured the mental state data. The mental state data can be tagged with an identity value for the individual. The mental state data can be reassembled, based on the tagging, allowing the combination of images collected from multiple devices. Analysis of the tagged data can allow the generation of an emotigraphic profile for an individual. The mental state data can be tagged with information on the context in which the mental state data was collected. The partitioning can separate the mental state data into two or more groups depending on the contents of the tags.

The flow 100 further comprises inferring mental states 130 based on the mental state data which was collected. Mental states that may be inferred may include one or more of a group including enjoyment, happiness, anger, sadness, stress, frustration, confusion, disappointment, hesitation, cognitive overload, focusing, being engaged, attending, boredom, exploration, confidence, trust, delight, and satisfaction. The mental state data can include one or more of smiles, laughter, smirks, or grimaces. The mental state data can include information based on the Facial Action Coding System (FACS). FACS is a detailed catalog of unique action units that correspond to independent motions of the face. FACS enables the measurement and scoring of facial activity in an objective, reliable, and quantitative way, and can be used to discriminate between subtle differences in facial motion. Various independent motions can be classified using action units; in embodiments, the mental state data includes FACS action units. The mental state data can include one or more of head position, up/down head motion, side-to-side head motion, tilting head motion, body leaning motion, or gaze direction. Various mental states can be inferred, and the mental states can comprise one or more of a group including frustration, confusion, disappointment, hesitation, cognitive overload, focusing, being engaged, attending, boredom, exploration, confidence, trust, delight, or satisfaction. Once mental states are inferred, the flow 100 further comprises populating a calendar 134 based on the mental states which were inferred. The populating can include placing mental state data, mental state information, or representations of mental states in a timeline or calendar for a viewer's benefit or review.

The flow 100 further comprises determining contextual information 132 related to the collected mental state data. Any type of contextual information related to the collection of the mental state data can be obtained. Some examples of collectible contextual information include a task assigned to the user, the location of the user, the environmental conditions that the user is exposed to—such as temperature, humidity, and the like—the name of the content being viewed, the level of noise experienced by the user, or any other type of contextual information. In some embodiments, the contextual information is based on one or more of skin temperature or accelerometer data. In some embodiments, the contextual information is based on one or more of a photograph, an email, a text message, a phone log, or GPS information.

The flow 100 includes rendering an output 140 based on the analysis of the mental state data. In various embodiments, the rendering can be graphical, pictorial, textual, auditory, or any combination thereof. The rendering can include an emotigraphic profile. The rendering can be presented on a local or remote electronic display. In some embodiments the rendering is printed on paper. The flow 100 further comprises posting information based on the analysis 142 to a social network page. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
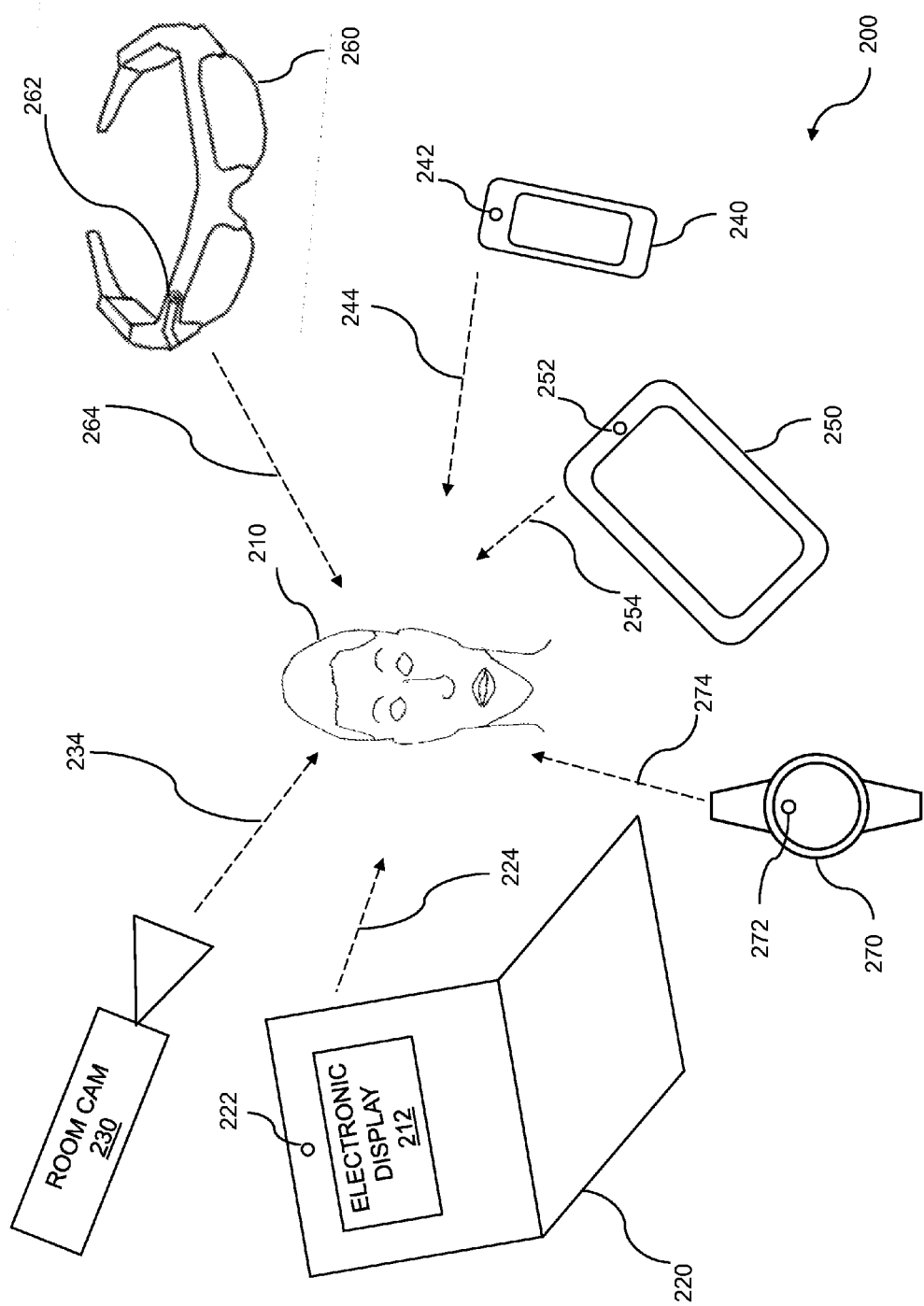
FIG. 2 is a diagram showing facial data collection from multiple devices.

FIG. 2 is a diagram 200 showing facial data collection from multiple devices. A user 210 could be performing a task, viewing a media presentation on an electronic display 212, or doing something else where it could prove useful to determine the user's mental state. The electronic display 212 can be on a laptop computer 220 as shown, a tablet computer 250, a cell phone 240, a desktop computer monitor, a television, or any other type of electronic device. The mental state data can be collected on a mobile device such as a cell phone 240, a tablet computer 250, a laptop computer 220, or a watch camera 270. Thus, the multiple sources can include at least one mobile device, such as a phone 240, a tablet 250, or a wearable device such as glasses 260. A mobile device can include a forward facing camera and/or rear facing camera that can be used to collect mental state data. The at least two sources of facial data can include one or more of a webcam 222, a phone camera 242, a tablet camera 252, a wearable camera 262, and a room camera 230. A wearable camera may be some other wearable camera device.

As the user 210 is monitored, the user 210 may move due to the nature of the task, boredom, distractions, or for another reason. As the user moves, the camera with a view of the user's face can change. Thus if the user 210 is looking in a first direction, the line of sight 224 from the webcam 222 is able to observe the individual's face, in certain embodiments, but if the user is looking in a second direction, the line of sight 234 from the room camera 230 is able to observe the individual's face. Further, in other embodiments, if the user is looking in a third direction, the line of sight 244 from the phone camera 242 is able to observe the individual's face, and if the user is looking in a fourth direction, the line of sight 254 from the tablet cam 252 is able to observe the individual's face. If the user is looking in a fifth direction, the line of sight 264 from the wearable camera 262, which may be a device such as the glasses 260 shown and can be worn by another user or an observer, is able to observe the individual's face. If the user is looking in a sixth direction, the line of sight 274 from the wearable watch-type device 270 with a camera 272 included on the device, is able to observe the individual's face. In other embodiments, the wearable device is a another device, such as an earpiece with a camera, a helmet or hat with a camera, a clip-on camera attached to clothing, or any other type of wearable device with a camera or other sensor for collecting mental state data. The individual 210 can also wear a wearable device including a camera that is used for gathering contextual information and/or collecting mental state data on other users. Because the individual 210 can move their head, the facial data can be collected intermittently when the individual is looking in a direction of a camera. In some cases, multiple people are included in the view from one or more cameras, and some embodiments include filtering out faces of one or more other people to determine whether the individual 210 is looking toward a camera. In some cases, multiple people may be included in the view from one or more cameras, and some embodiments include filtering out faces of one or more other people to determine whether the individual 210 is looking toward a camera. All or some of the mental state data may be sporadically available from these various devices.

Figure 3:
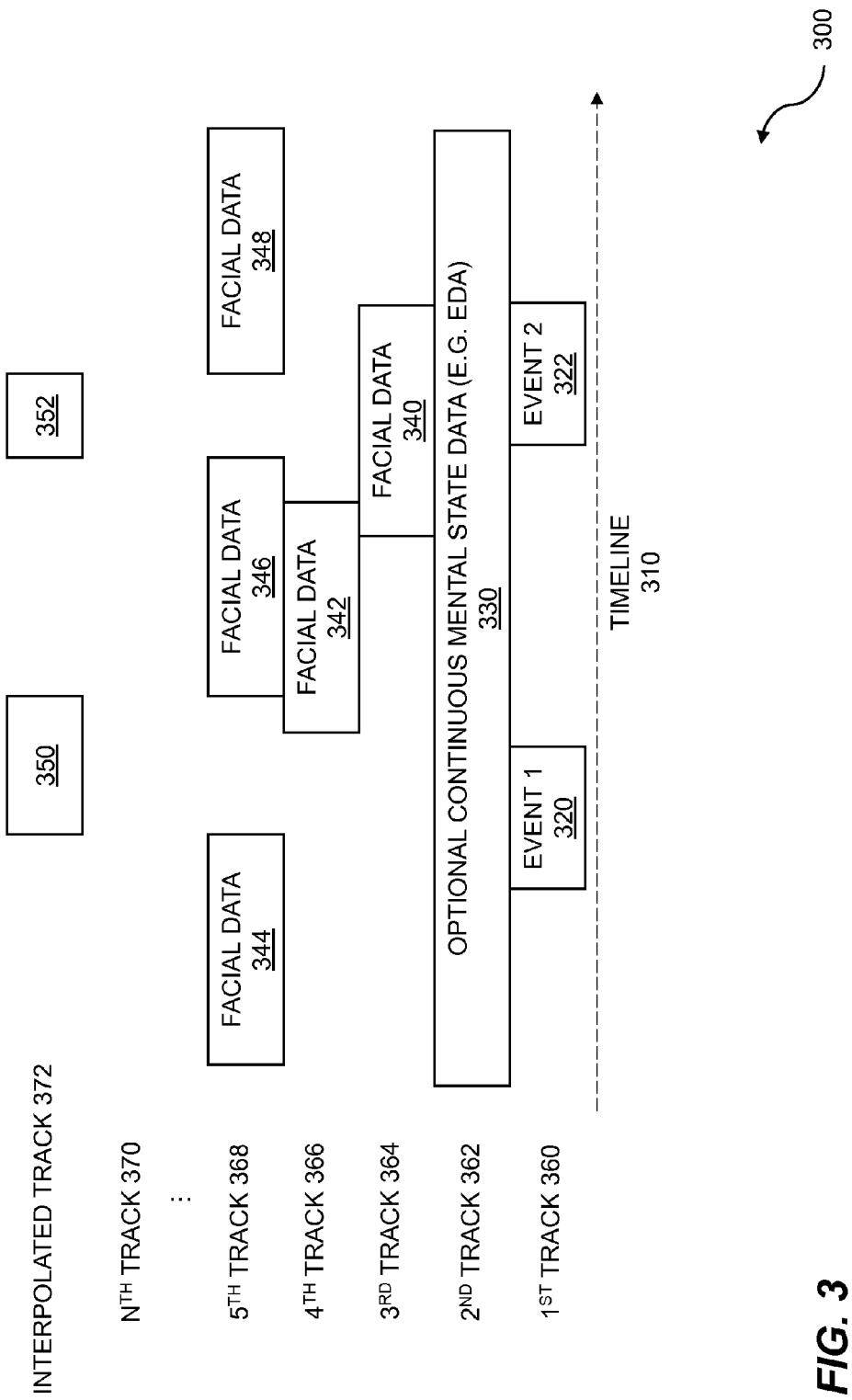
FIG. 3 is a timeline with information tracks relating to mental states.

FIG. 3 is a timeline 310 with information tracks 300 relating to mental states. A first track 360 shows events that, in embodiments, are related to the individual's use of a computer. A first event 320 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply save contextual information in the first track 360. A second event 322 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 362 can include continuously collected mental state data such as electrodermal activity data 330. A third track 364 can include facial data, which, in embodiments, is a type of mental state data that is collected on an intermittent basis by a first camera, such as the room cam 230 of FIG. 2 (although in some embodiments the facial data is collected continuously). The facial data can be collected intermittently when the individual is looking toward a camera. The facial data 340 can include one or more still photographs, videos, or abstracted facial expressions which can be collected when the user looks in the direction of the camera. A fourth track 366 can include facial data that is collected on an intermittent or continuous basis by a second camera, such as the mobile phone camera 242 of FIG. 2. The facial data 342 can include one or more still photographs, videos, or abstracted facial expressions which can be collected when the user looks in the direction of that camera. A fifth track 368 can include facial data that is collected from a third camera, such as the webcam 222 of FIG. 2. In the example shown, the fifth track 368 includes first facial data 344, second facial data 346, and third facial data 348, which can be any type of facial data including data that can be used for determining mental state information. Any number of samples of facial data can be collected in any track. The mental state data from the various tracks can be collected simultaneously, collected on one track exclusive of other tracks, collected where mental state data overlaps between the tracks, and so on. When mental state data from multiple tracks overlap, one track's data can take precedence or the data from the multiple tracks can be combined.

Additional tracks, through the n$^{th}$ track 370, of mental state data of any type can be collected. The additional tracks 370 can be collected on a continuous or on an intermittent basis. The intermittent basis can be either occasional or periodic. Analysis can further comprise interpolating mental state data when the mental state data collected is intermittent, and/or imputing additional mental state data where the mental state data is missing. One or more interpolated tracks 372 can be included and can be associated with mental state data that is collected on an intermittent basis, such as the facial data of the fifth track 368. Interpolated data 350 and interpolated data 352 can contain interpolations of the facial data of the fifth track 368 for the time periods where no facial data was collected in that track. Other embodiments interpolate data for periods where no track includes facial data. In other embodiments, analysis includes interpolating mental state analysis when the mental state data collected is intermittent.

The mental state data, such as the continuous mental state data 330 and/or any of the collected facial data 340, 342, 344, 346, and 348, can be tagged. The tags can include metadata related to the mental state data, including, but not limited to, the device that collected the mental state data; the individual from whom the mental state data was collected; the task being performed by the individual; the media being viewed by the individual; and the location, environmental conditions, time, date, or any other contextual information. The tags can be used to locate pertinent mental state data; for example, the tags can be used to retrieve the mental state data from a database. The tags can be included with the mental state data that is sent over the internet to cloud or web-based storage and/or services; so, the tags can be used locally on the machine where the mental state data was collected and/or remotely on a remote server or a cloud/web service.

Figure 4:
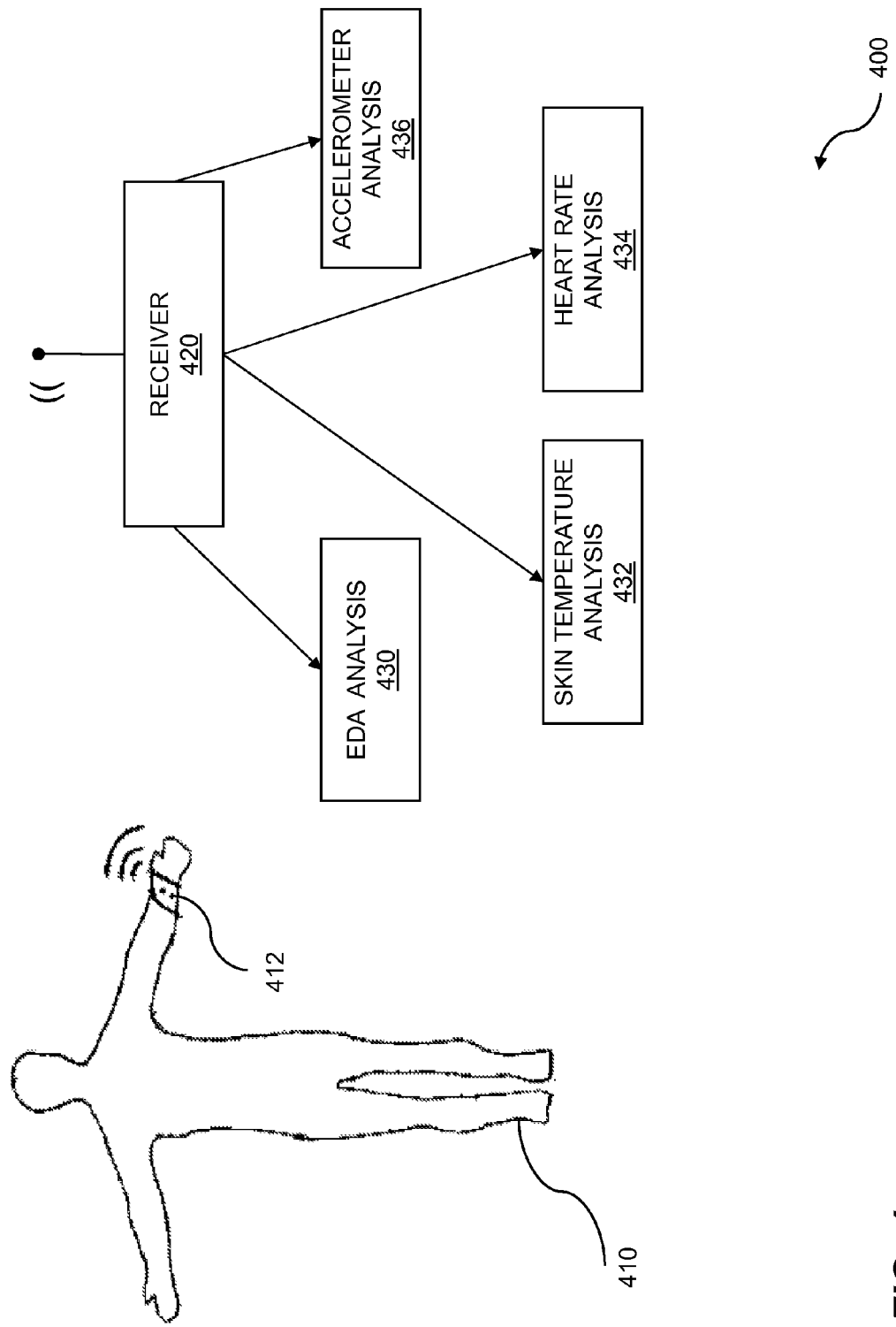
FIG. 4 is diagram for sensor analysis.

FIG. 4 is a diagram for sensor analysis. A system 400 can analyze data collected from a person 410 as he or she interacts with a computer or views a media presentation. The person 410 can have a biosensor 412 attached to him or her for the purpose of collecting mental state data. The biosensor 412 can be placed on the wrist, palm, hand, head, or other part of the body. In some embodiments, multiple biosensors are placed on the body in multiple locations. The biosensor 412 can include detectors for physiological data such as electrodermal activity, skin temperature, accelerometer readings, and the like. Other detectors for physiological data can also be included, such as heart rate, blood pressure, EKG, EEG, other types of brain waves, and other physiological detectors. The biosensor 412 can transmit collected information to a receiver 420 using wireless technology such as Wi-Fi, Bluetooth, 802.11, cellular, or other bands. In other embodiments, the biosensor 412 communicates with the receiver 420 using other methods such as a wired or optical interface. The receiver can provide the data to one or more components in the system 400. In some embodiments, the biosensor 412 records multiple types of physiological information in memory for later download and analysis. In some embodiments, the download of recorded physiological data is accomplished through a USB port or other form of wired or wireless connection.

Mental states can be inferred based on physiological data, such as physiological data from the sensor 412. Mental states can also be inferred based on facial expressions and head gestures observed by a webcam, or using a combination of data from the webcam and data from the sensor 412. The mental states can be analyzed based on arousal and valence. Arousal can range from being highly activated—such as when someone is agitated—to being entirely passive—such as when someone is bored. Valence can range from being very positive—such as when someone is happy—to being very negative—such as when someone is angry. Physiological data can include one or more of electrodermal activity (EDA), heart rate, heart rate variability, skin temperature, respiration, accelerometer readings, and other types of analysis of a human being. It will be understood that both here and elsewhere in this document physiological information can be obtained either by biosensor 412 or by facial observation via an image capturing device. Facial data can include facial actions and head gestures used to infer mental states. Further, the data can include information on hand gestures or body language and body movements such as visible fidgets. In some embodiments, these movements are captured by cameras, while in other embodiments, these movements are captured by sensors. Facial data can include the tilting the head to the side, leaning forward, smiling, frowning, and many other gestures or expressions.

In some embodiments, electrodermal activity is collected, either continuously, every second, four times per second, eight times per second, 32 times per second, or on some other periodic basis. Or, in some embodiments, electrodermal activity is collected on an intermittent basis. The electrodermal activity can be recorded and stored onto a disk, a tape, flash memory, a computer system, or streamed to a server. The electrodermal activity can be analyzed 430 to indicate arousal, excitement, boredom, or other mental states based on observed changes in skin conductance. Skin temperature can be collected and/or recorded on a periodic basis. In turn, the skin temperature can be analyzed 432. Changes in skin temperature can indicate arousal, excitement, boredom, or other mental states. Heart rate information can be collected and recorded, and can also be analyzed 434. A high heart rate can indicate excitement, arousal, or other mental states. Accelerometer data can be collected and used to track one, two, or three dimensions of motion. The accelerometer data can be recorded. The accelerometer data can be used to create an actigraph showing an individual's activity level over time. The accelerometer data can be analyzed 436 and can indicate a sleep pattern, a state of high activity, a state of lethargy, or other states. The various data collected by the biosensor 412 can be used along with the facial data captured by the webcam in the analysis of mental states. Contextual information can be based on one or more of skin temperature and/or accelerometer data. The mental state data can include one or more of a group including physiological data, facial data, and accelerometer data.

Figure 5:
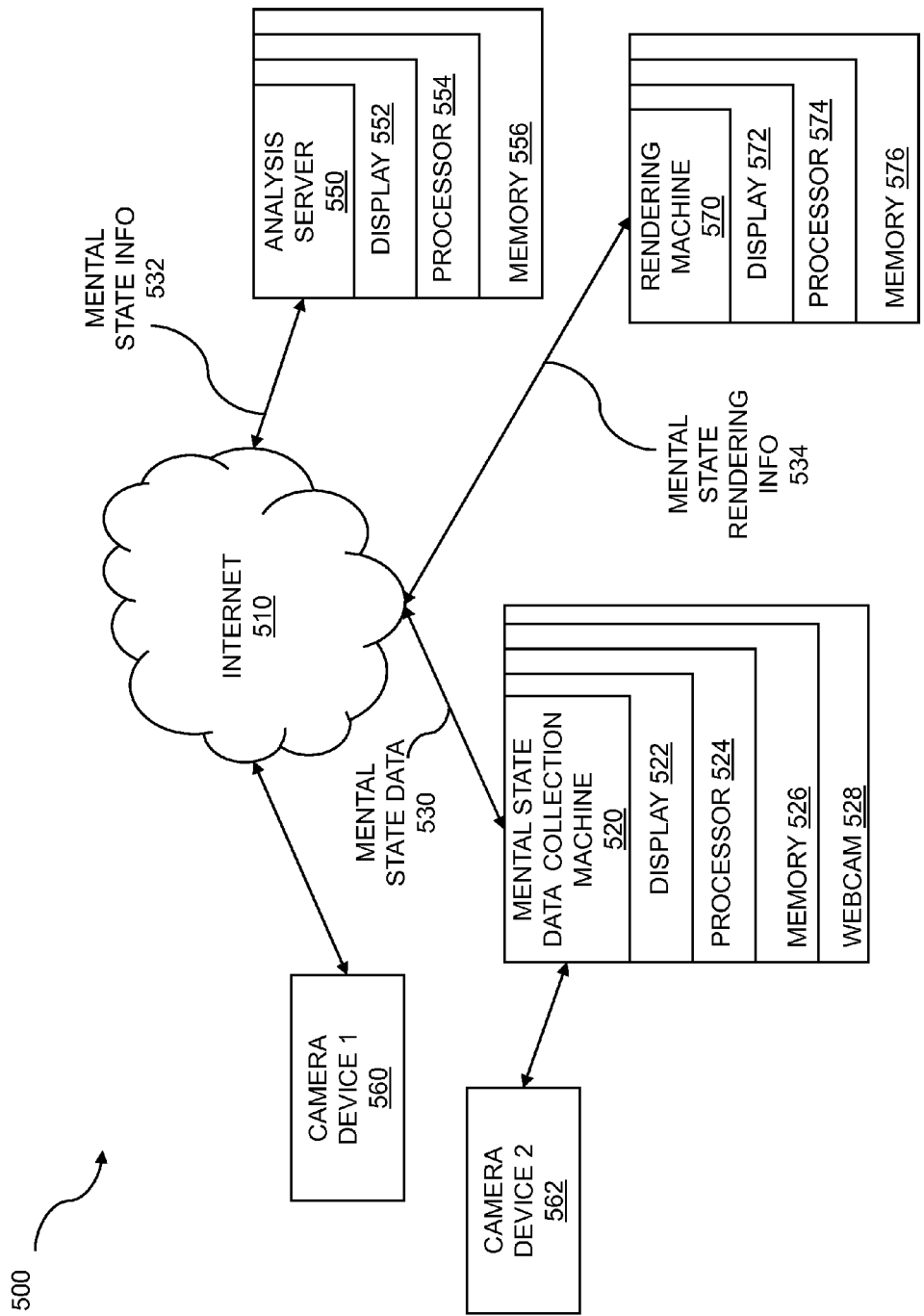
FIG. 5 is a system diagram for mental state analysis.

FIG. 5 is a system diagram for mental state analysis. The system 500 can include one or more computers coupled together by a communication link such as the Internet 510. The system 500 can also include two or more cameras that can be linked to the one or more computers and/or directly to a communication link. The system 500 can include a mental state data collection machine 520, which, in some embodiments, is also referred to as a client machine. The mental state data collection machine 520 includes a memory 526 which stores instructions, one or more processors 524 coupled to the memory, a display 522, and a webcam 528. The display 522 may be any electronic display, including but not limited to, a computer display, a laptop screen, a net-book screen, a tablet screen, a cell phone display, a mobile device display, a remote with a display, a television, a projector, or the like. The webcam 528, as the term is used herein, may refer to a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by an electronic system.

An individual can interact with the mental state data collection machine 520, interact with another computer, or view a media presentation on another electronic display, among other activities. The system 500 may include a computer program product embodied in a non-transitory computer readable medium including code for obtaining mental state data which is collected on an individual from multiple sources wherein the multiple sources include at least two sources of facial data, code for obtaining analysis of the mental state data which is collected from multiple sources, and code for rendering an output based on the analysis of the mental state data. With such a program stored in memory, the one or more processors 524 can be configured to obtain mental state data which is collected on the individual from multiple sources wherein the multiple sources include at least two sources of facial data, obtain analysis of the mental state data which is collected from multiple sources, and render an output based on the analysis of the mental state data. Thus the system 500 can enable a method for collecting mental state data on an individual from multiple sources wherein the multiple sources include at least two sources of facial data, analyzing the mental state data which is collected from multiple sources, and rendering an output based on the analysis of the mental state data. The multiple sources can include two or more of the webcam 528, a first camera device 560 linked through the internet 510, and/or a second camera device 562 linked directly to the mental state data collection machine 520. In some embodiments, the mental state data collection machine 520 can send mental state data 530 to another computer, such as the analysis server 550.

Some embodiments can include a web service or analysis server 550. The analysis server 550 includes one or more processors 554 coupled to a memory 556 to store instructions. Some embodiments of the analysis server 550 include a display 552. The one or more processors 554 can be configured to receive mental state data from the mental state data collection machine 530, the first camera device 560, and/or other computers configured to collect mental state data; the mental state data can include data from at least two sources that can be coupled to one or more machines. The one or more processors 554 can then analyze the mental state data received and provide mental state information 532. The analysis can produce mental state information, inferred mental states, emotigraphs, actigraphs, other textual/graphical representations, or any other type of analysis. In some embodiments, analysis of the mental state data is augmented by a human coder. The analysis server 550 can display at least some of the analysis on the display 552 and/or can provide the analysis of the mental state data to a client machine such as the mental state data collection machine 520 or another client machine 570 to be displayed to a user. So, the system 500 can enable a method for receiving mental state data which is collected on an individual from multiple sources, wherein the multiple sources include at least two sources of facial data, analyzing the mental state data which is collected from multiple sources, and providing the analysis of the mental state data to a rendering or client machine 570. In some embodiments, the analysis server 550 can be provisioned as a web server with the analysis of the mental state data obtained from a web service.

Some embodiments include a rendering or second client machine 570. The rendering machine 570 includes one or more processors 574 coupled to memory 576 to store instructions, and a display 572. The client machine can receive the analysis of the mental state data from the analysis server 550 and can render an output to the display 572. The system 500 can enable a computer-implemented method for mental state analysis comprising receiving analysis of mental state data which is collected on an individual from multiple sources wherein the multiple sources include at least two sources of facial data and rendering an output based on the analysis of the mental state data.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
    obtaining mental state data which is collected on an individual from multiple sources wherein the multiple sources include at least two sources of facial image data, wherein at least one of the facial image data sources collects facial image data intermittently while the individual is looking toward a camera, and wherein the multiple sources include at least one mobile device, including a cell phone, a tablet computer, or a wearable device;
    aggregating, using one or more processors, the mental state data from the multiple sources;
    obtaining analysis of the mental state data which is aggregated from the multiple sources, wherein the analysis results in mental state analysis;
    interpolating the mental state analysis where the mental state data collected is intermittent, wherein the interpolating generates interpolated data for time periods during which mental state data was not collected from one or more of the multiple sources; and
rendering an output based on the analysis of the mental state data.

2. The method of claim 1 wherein the mental state data from multiple sources is tagged.

3. The method of claim 2 wherein the mental state data is tagged with an identity value for the individual.

4. The method of claim 3 wherein the mental state data is tagged with information on context in which the mental state data was collected.

5. The method of claim 2 further comprising partitioning the mental state data based on tagging.

6. The method of claim 1 wherein the at least two sources of the facial image data include one or more of a webcam, a phone camera, a tablet camera, a wearable camera, a room camera, a mobile device, a cell phone, a tablet computer, or a laptop computer.

7. The method of claim 1 wherein the at least one mobile device includes a forward facing camera.

8. The method of claim 1 wherein the analysis of the mental state data is obtained from a web service.

9. The method of claim 1 further comprising performing face detection to determine whether the individual is looking toward the camera.

10. The method of claim 9 further comprising filtering out faces of one or more other people to determine whether the individual is looking toward the camera.

11. The method of claim 1 further comprising interpolating mental state data when the mental state data collected is intermittent.

12. The method of claim 1 further comprising imputing additional mental state data for one or more periods where no mental state data was collected.

13. The method of claim 1 further comprising determining contextual information.

14. The method of claim 13 wherein the contextual information is based on one or more of skin temperature, accelerometer data, a photograph, an email, a text message, a phone log, or GPS information.

15. The method of claim 1 further comprising inferring mental states based on the mental state data which was collected.

16. The method of claim 15 wherein the mental states inferred include one or more of frustration, confusion, disappointment, hesitation, cognitive overload, focusing, being engaged, attending, boredom, exploration, confidence, trust, delight, or satisfaction.

17. The method of claim 16 further comprising populating a calendar based on the mental states which were inferred.

18. The method of claim 1 further comprising posting information based on the analysis to a social network page.

19. The method of claim 1 wherein the mental state data includes one or more of a group including physiological data, facial image data, or accelerometer data.

20. The method of claim 19 wherein the physiological data includes one or more of electrodermal activity, heart rate, heart rate variability, skin temperature, or respiration.

21. A computer program product embodied in a non-transitory computer readable medium for mental state analysis, the computer program product comprising code which causes one or more processors to perform operations of:
obtaining mental state data which is collected on an individual from multiple sources wherein the multiple sources include at least two sources of facial image data, wherein at least one of the facial image data sources collects facial image data intermittently while the individual is looking toward a camera, and wherein the multiple sources include at least one mobile device, including a cell phone, a tablet computer, or a wearable device;
aggregating the mental state data from the multiple sources;
obtaining analysis of the mental state data which is aggregated from multiple sources, wherein the analysis results in mental state analysis;
interpolating the mental state analysis where the mental state data collected is intermittent, wherein the interpolating generates interpolated data for time periods during which mental state data was not collected from one or more of the multiple sources; and
rendering an output based on the analysis of the mental state data.

22. A computer system for mental state analysis comprising:
a memory which stores instructions;
one or more processors coupled to the memory wherein the one or more processors, when executing the instructions which are stored, are configured to:
obtain mental state data which is collected on an individual from multiple sources wherein the multiple sources include at least two sources of facial image data, wherein at least one of the facial image data sources collects facial image data intermittently while the individual is looking toward a camera, and wherein the multiple sources include at least one mobile device, including a cell phone, a tablet computer, or a wearable device;
aggregate the mental state data from the multiple sources;
obtain analysis of the mental state data which is aggregated from multiple sources, wherein the analysis results in mental state analysis;
interpolate the mental state analysis where the mental state data collected is intermittent, wherein the interpolation generates interpolated data for time periods during which mental state data was not collected from one or more of the multiple sources; and
render an output based on the analysis of the mental state data.

23. The method of claim 1 wherein the facial image data includes abstracted facial expression information.

24. The method of claim 1 wherein the facial image data is used to determine mental state information.

25. The method of claim 1 further comprising stitching mental state analysis from the mental state data from the multiple sources.

26. The method of claim 25 wherein the mental state analysis further comprises identifying a best view, from the multiple sources of facial image data, and stitching the mental state analysis together based on the best view that was identified for the mental state data that was collected intermittently.

27. The method of claim 5 wherein the partitioning of the mental state data is based on tags identifying a source of the intermittent mental state data.

28. The method of claim 2 further comprising analyzing the mental state data that was tagged to generate an emotigraphic profile for the individual.

29. The method of claim 5 further comprising separating the mental state data into two or more groups based on content of tags from the mental state data that was tagged.

30. The method of claim 29 further comprising reassembling the mental state data, based on the tags.

31. The method of claim 30 wherein the reassembling allows combining of images collected from multiple devices.

32. The method of claim 1 wherein the output is used to populate a calendar along with activities already included in the calendar.

33. The method of claim 1 wherein the interpolating generates interpolated data for a first one of the multiple sources for time periods during which mental state data was not collected from the first one of the multiple sources.

34. The method of claim 1 wherein the interpolating generates interpolated data for time periods during which mental state data was not collected from any of the multiple sources.

35. The method of claim 1 wherein the interpolating generates interpolated data as a function of mental state data collected from at least two of the multiple sources.

* * * * *